(12) United States Patent
Yeh

(10) Patent No.: US 6,418,395 B1
(45) Date of Patent: Jul. 9, 2002

(54) METHOD FOR SETTING THE MEASURING STATE OF A HAEMADYNAMOMETER

(76) Inventor: Michael Yeh, 2F, No. 8, Alley 20, Lane 106, Sec. 3, Nan Kang Rd., Taipei (TW)

( * ) Notice: Subject to any disclaimer, the term of this patent is extended or adjusted under 35 U.S.C. 154(b) by 0 days.

(21) Appl. No.: 09/421,563

(22) Filed: Oct. 20, 1999

(51) Int. Cl.[7] .................................................. G01L 15/00
(52) U.S. Cl. .................................... 702/139; 702/127
(58) Field of Search ..................................... 702/127, 139; 600/513, 480, 485, 454, 475, 484

(56) References Cited

U.S. PATENT DOCUMENTS

| | | | | |
|---|---|---|---|---|
| 4,129,124 A | * | 12/1978 | Thalmann .................. | 600/479 |
| 4,129,125 A | * | 12/1978 | Lester et al. ................ | 600/484 |
| 4,869,262 A | * | 9/1989 | Orr et al. .................... | 600/485 |
| 4,898,180 A | * | 2/1990 | Farrelly et al. ............. | 600/494 |
| 4,907,596 A | * | 3/1990 | Schmid et al. .............. | 600/485 |
| 4,944,304 A | * | 7/1990 | Nishina ....................... | 600/480 |
| 5,316,008 A | * | 5/1994 | Suga et al. .................. | 600/513 |
| 5,845,235 A | * | 12/1998 | Luukkanen et al. ........ | 702/127 |
| 6,027,453 A | * | 2/2000 | Miwa et al. ................. | 600/485 |
| 6,290,650 B1 | * | 9/2001 | Butterfield et al. ......... | 600/485 |

* cited by examiner

*Primary Examiner*—Marc S. Hoff
*Assistant Examiner*—Felix Suarez
(74) *Attorney, Agent, or Firm*—Rosenberg, Klein & Lee

(57) ABSTRACT

A method for setting the measuring states of a haemadynamometer comprises the steps of: actuating the power of the haemadynamometer; measuring blood pressure and displaying the measuring value; selecting the setting or unsetting various states according to the condition of the measurer, and displaying the state values; and finally, accessing the measuring values and the data of state values. Thereby, by the electronic haemadynamometer, the states of the user can be recorded. Then data can be look up from the haemadynamometer directly, or the data can be output to a PC for further analyzing so as to be as a reference of doctors.

3 Claims, 4 Drawing Sheets

| MEASURING TIME | PALPITATION | DIASTOLIC PRESSURE | SYSTOLIC PRESSURE | TEMPERATURE | MEASURING STATE |
|---|---|---|---|---|---|
| 07-28 12:30 | 68 | 68 | 168 | 32c | DRINK, TINNITUS |
| 07-29 08:26 | 65 | 82 | 137 | 28c | JUST GET OUT OF BED |
| 07-30 18:54 | 72 | 95 | 163 | 29c | AFTER EXERCISING |
| 07-31 23:10 | 68 | 85 | 137 | 26c | AFTER BATHING |

FIG. 4

METHOD FOR SETTING THE MEASURING
STATE OF A HAEMADYNAMOMETER

FIELD OF THE INVENTION

The present invention relates to a method for setting the measuring state of a haemadynamometer, and especially to a method for display and recording the states of one the blood pressure of which will be measured.

BACKGROUND OF THE INVENTION

The current electronic haemadynamometers only have the function of recording the blood pressure of users but not installed with the function for displaying the measuring states of those to be measured. The so-called "state" means the conditions of those to be measured. The state includes a physiological and psychological conditions, for example, before eating, after eating, before bathing, after bathing, in emotional condition, etc, uncomfortable in body, such as, dizzy, tinnitus, breast ache, headache, difficult in breathing, etc; before eating drugs, after eating drugs, etc.; before exercising, after exercising, after smoking; eating alcohol or coffee, etc. Moreover, it may be environmental condition in measurement, for example, temperature, humidity, measuring time, etc. All the conditions that effect blood pressure can be rocorded.

However, there are many abnormalities that affect blood pressure. If one may record these factors in daily life and the measurement value, this will be helpful to the judgement of doctors.

SUMMARY OF THE INVENTION

Therefore, the primary object of the present invention is to provide a method for setting the measuring state of a haemadynamometer which may record the display and recording the states of those to be measured.

Accordingly, the object of the present invention is to provide a method for setting the measuring state of a haemadynamometer. The method comprises the steps of: actuating the power of the haemadynamometer; measuring blood pressure and displaying the measuring value; selecting the setting or unsetting various states according to the condition of the measurer, and displaying the state values; and finally, accessing the measuring values and the data of state values. Thereby, by the electronic haemadynamometer, the states of the user can be recorded. Then data can be look up from the haemadynamometer directly, or the data can be output to a PC for further analyzing for being referred by a doctor.

The various objects and advantages of the present invention will be more readily understood from the following detailed description when read in conjunction with the appended drawing.

BRIEF DESCRIPTION OF THE DRAWINGS

FIG. 4 is a table shows the measuring result of a haemadynamometer.

DETAILED DESCRIPTION OF THE PREFERRED EMBODIMENTS

Figure 1:
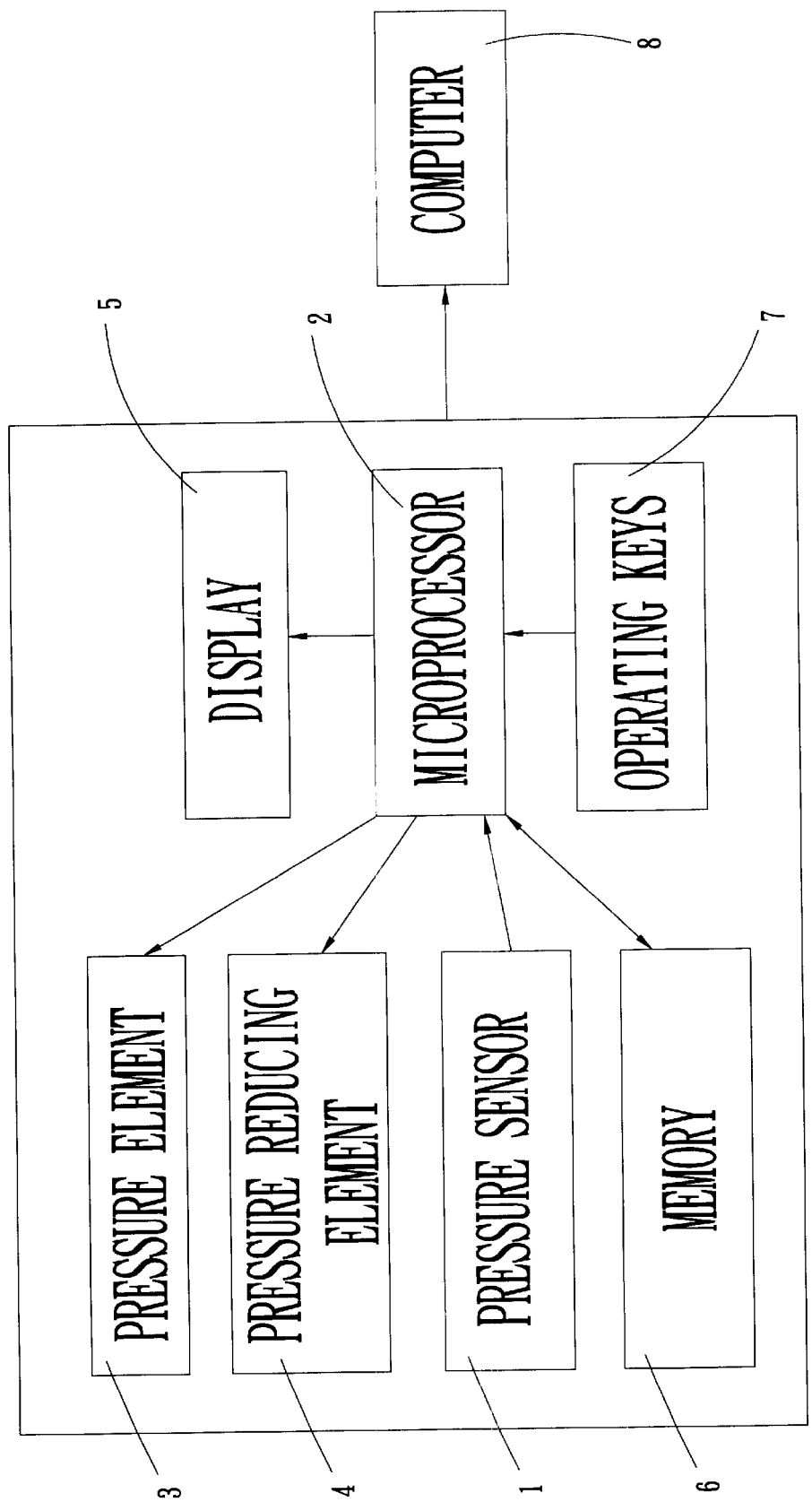
FIG. 1 shows the elements of a haemadynamometer according to the present invention.
Figure 2:
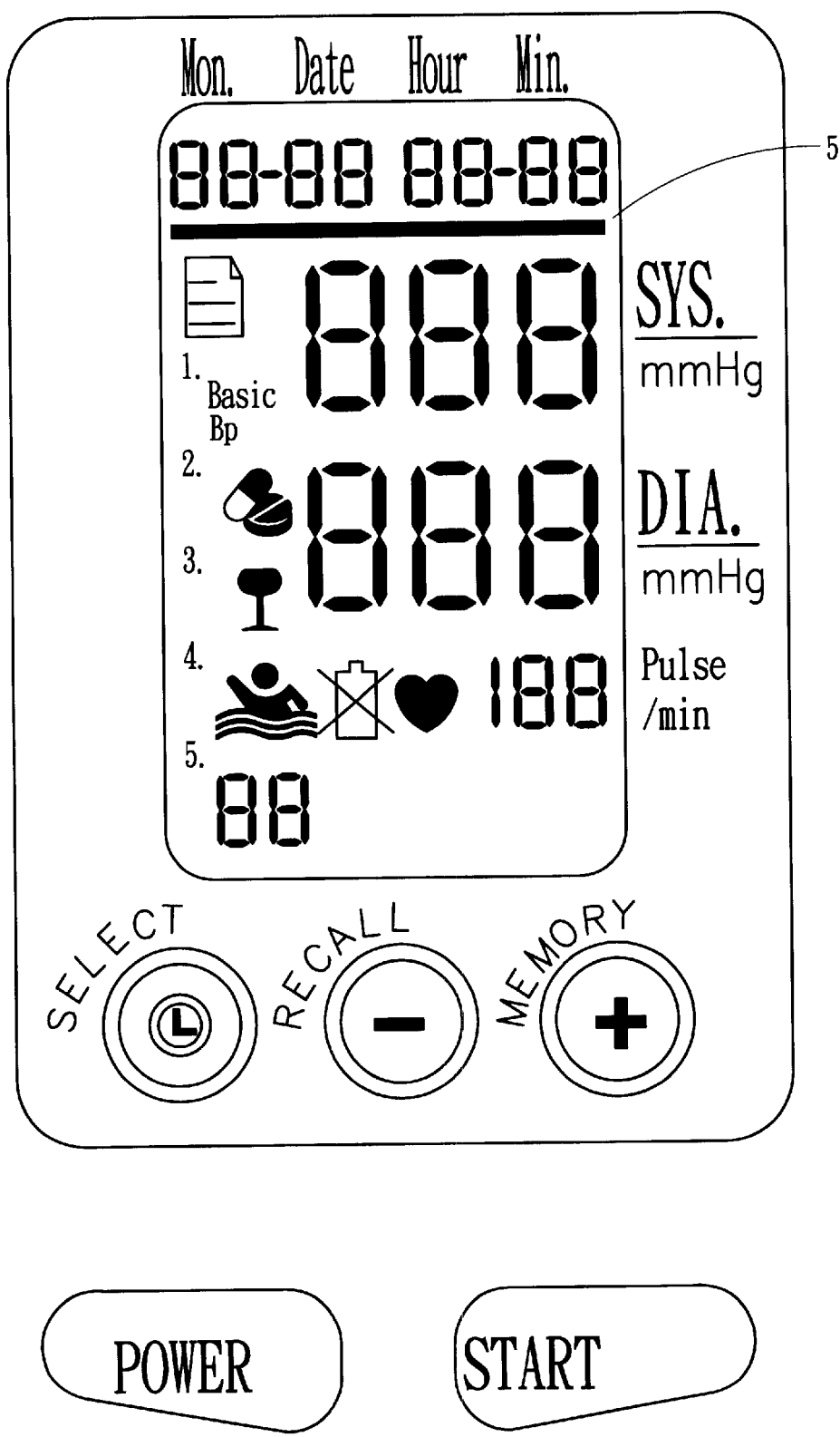
FIG. 2 shows the panel of the haemadynamometer according to the present invention.

With reference to FIGS. 1 and 2, the relative elements of the haemadynamometer according to the present invention is illustrated. The haemadynamometer includes a pressure sensor 1, a microprocessor (CPU) 2, a pressure element 3, a pressure reducing element 4, a display 5, a memory 6, an operating button 7, a computer 8, etc.

The pressure sensor 1 transfers the sensing results to the microprocessor 2. According to this message, the microprocessor 2 drives the pressure element 3 and the pressure reducing element 4 to derive the measurement value of blood pressure which is then displayed on the display 5. Meanwhile, the database of the memory 6 is actuated to show possible states. Then the state selected by the measurer and the measurement value are stored in the memory 6. Finally, the memory data in the memory 6 is sent to the PC 8 for further analyzing.

Figure 3:
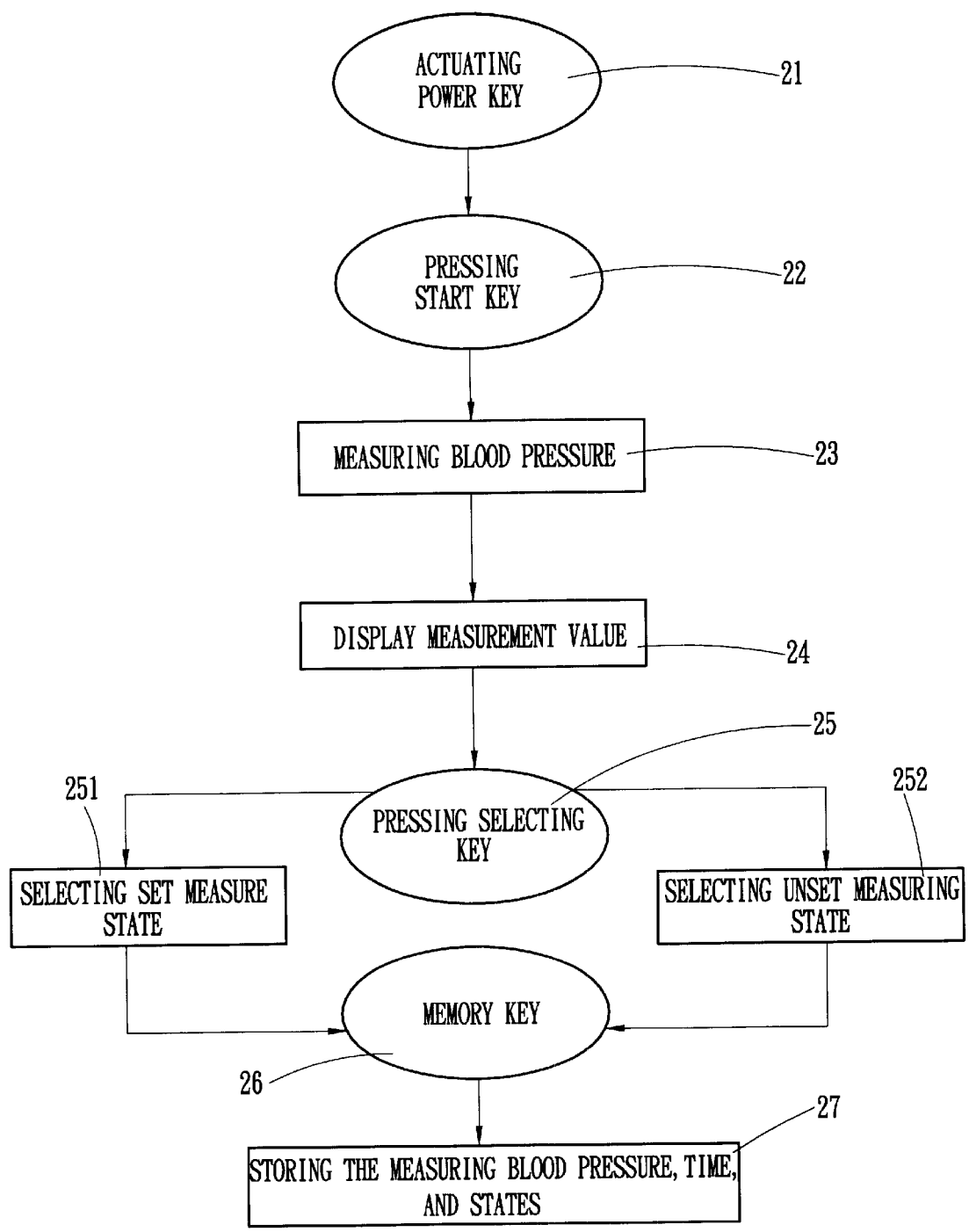
FIG. 3 shows the flow diagram of the haemadynamometer according to the present invention for recording the operation of states.

Referring to FIG. 3, a flow diagram about the haemadynamometer of the present invention recording the state is illustrated.

At first, the user presses a power key (step 21) to actuate the power of the haemadynamometer.

An optimum pose is adjusted, and then the state key (step 22) is pressed. The haemadynamometer starts to measure (step 23). As the measurement is over, the haemadynamometer will display the measuring results on the display Then, pressing a select key 25, the display will show various states for being selected. The user may select the states according to the conditions. Namely, if a set measure state 251 is selected, the display will show the state values of items 1 to 4. If an unset measure state 252 is selected, the display will show the state value of item 5.

Finally, the memory key 26 is pressed, the measurement value and the selected state value is stored in the memory region of the haemadynamometer (step 27). The state value in the haemadynamometer can be directly to the PC 8 for further analyzing (or the displayed air state value data can be searched for the haemadynamometer), therefore, the whole operation process is complete.

With reference to FIG. 4, a table about the operation of the haemadynamometer according to the present invention is illustrated. The measuring results of the user in some states (such as drink, tinnitus, get out of bed, after exercising, after bathing, etc) about the measuring time, palpitation, diastolic pressure, systolic pressure, temperature, and measuring states.

Therefore, in the present invention, by an electronic haemadynamometer, the states of the user can be recorded. Then data can be look up from the haemadynamometer directly, or the data can be output to a PC for further analyzing to be as a reference of doctors.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A method for setting a measuring state of a haemadynamometer, comprising the steps of:
   a. actuating a power switch of the haemadynamometer;
   b. measuring a user's blood pressure and displaying measured blood pressure values;
   c. selecting at least one of a plurality of measuring states pre-stored in a memory of the haemadynamometer from a display of said plurality of measuring states;
   d. storing said measured blood pressure values and said selected at least one measuring state associated therewith in the memory;

e. repeating steps a–e at least once; and, f. supplying said stored blood pressure values and associated measuring states to a computer for analysis.

2. The method as recited in claim 1, wherein the step of repeating includes the step of selecting at least one measuring state different from said at least one measuring state selected previously in step c.

3. The method as recited in claim 1, wherein the step of selecting at least one of a plurality of measuring states is preceded by the step of pre-storing measuring states selected from the group consisting of drinking, tinnitus, arisen from bed, after exercising, after bathing, and after medication.

* * * * *